US010251804B2

(12) United States Patent
Sugata

(10) Patent No.: US 10,251,804 B2
(45) Date of Patent: Apr. 9, 2019

(54) WALKING TRAINING APPARATUS AND WALKING TRAINING METHOD THEREFOR

(71) Applicant: TOYOTA JIDOSHA KABUSHIKI KAISHA, Toyota-shi (JP)

(72) Inventor: Hikaru Sugata, Miyoshi (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 0 days.

(21) Appl. No.: 15/263,025

(22) Filed: Sep. 12, 2016

(65) Prior Publication Data

US 2017/0071813 A1    Mar. 16, 2017

(30) Foreign Application Priority Data

Sep. 10, 2015   (JP) ................................. 2015-178278

(51) Int. Cl.
*A63B 69/00* (2006.01)
*A61H 3/00* (2006.01)
(Continued)

(52) U.S. Cl.
CPC .................. *A61H 3/00* (2013.01); *A61B 5/11* (2013.01); *A61H 1/024* (2013.01); *A61H 1/0244* (2013.01); *A61H 3/008* (2013.01); *A63B 21/00181* (2013.01); *A63B 21/4027* (2015.10); *A63B 22/02* (2013.01); *A63B 22/0242* (2013.01); *A63B 23/03516* (2013.01); *A63B 23/04* (2013.01); *A63B 24/0087* (2013.01); *G09B 5/02* (2013.01); *G09B 19/003* (2013.01); *A61H 1/0262* (2013.01); *A61H 1/0266* (2013.01);
(Continued)

(58) Field of Classification Search
CPC .................................................. A63B 69/0028
See application file for complete search history.

(56) References Cited

U.S. PATENT DOCUMENTS 6,569,065 B1 * 5/2003 Menold ............. A63B 22/0076
                                                                482/127
6,835,167 B2 * 12/2004 Schmidt ............. A63B 21/0058
                                                                482/51
(Continued)

FOREIGN PATENT DOCUMENTS

JP        2012-95793 A      5/2012

*Primary Examiner* — Loan H Thanh
*Assistant Examiner* — Rae Fischer
(74) *Attorney, Agent, or Firm* — Oblon, McClelland, Maier & Neustadt, L.L.P.

(57) ABSTRACT

A walking training apparatus includes a walking assistance apparatus for a leg of a trainee, a first wire winding mechanism for pulling a wire for the leg upward and forward, pulling control means for controlling the first wire winding mechanism to pull the wire with a first pulling force, and storage amount detection means for detecting a storage amount of the wire. The pulling control means controls the first wire winding mechanism so that the first wire winding mechanism pulls the wire with a second pulling force larger than the first pulling force in a swinging start period in which the storage amount of the wire detected by the storage amount detection means is equal to or smaller than a predetermined storage amount of the wire in a period including a timing when the wire of the first wire winding mechanism changes from a pulling-out state to a winding state.

8 Claims, 9 Drawing Sheets

(51) Int. Cl.
  *A61H 1/02*   (2006.01)
  *A63B 21/00*   (2006.01)
  *A63B 23/035*   (2006.01)
  *A63B 23/04*   (2006.01)
  *A63B 24/00*   (2006.01)
  *G09B 19/00*   (2006.01)
  *A61B 5/11*   (2006.01)
  *A63B 22/02*   (2006.01)
  *G09B 5/02*   (2006.01)
  *A63B 71/06*   (2006.01)
  *A63B 71/00*   (2006.01)

(52) U.S. Cl.
  CPC .................. *A61H 2003/007* (2013.01); *A61H 2201/0176* (2013.01); *A61H 2201/0192* (2013.01); *A61H 2201/1215* (2013.01); *A61H 2201/1261* (2013.01); *A61H 2201/14* (2013.01); *A61H 2201/1463* (2013.01); *A61H 2201/163* (2013.01); *A61H 2201/164* (2013.01); *A61H 2201/165* (2013.01); *A61H 2201/1621* (2013.01); *A61H 2201/1652* (2013.01); *A61H 2201/1676* (2013.01); *A61H 2201/5007* (2013.01); *A61H 2201/5043* (2013.01); *A61H 2201/5048* (2013.01); *A61H 2201/5061* (2013.01); *A61H 2201/5069* (2013.01); *A61H 2201/5071* (2013.01); *A61H 2201/5079* (2013.01); *A61H 2230/80* (2013.01); *A63B 21/153* (2013.01); *A63B 21/4007* (2015.10); *A63B 21/4009* (2015.10); *A63B 21/4011* (2015.10); *A63B 69/0057* (2013.01); *A63B 71/0622* (2013.01); *A63B 2024/0093* (2013.01); *A63B 2071/0081* (2013.01); *A63B 2071/065* (2013.01); *A63B 2071/0625* (2013.01); *A63B 2071/0647* (2013.01); *A63B 2207/02* (2013.01); *A63B 2220/13* (2013.01); *A63B 2220/24* (2013.01); *A63B 2220/34* (2013.01); *A63B 2220/50* (2013.01); *A63B 2220/51* (2013.01); *A63B 2220/56* (2013.01); *A63B 2220/806* (2013.01); *A63B 2220/807* (2013.01); *A63B 2220/833* (2013.01); *A63B 2220/836* (2013.01); *A63B 2230/01* (2013.01)

(56) References Cited

U.S. PATENT DOCUMENTS 7,524,272 B2 *   4/2009   Bruck .................. A63B 21/153
                   482/126
7,857,779 B2 *   12/2010   Gondringer ............ A61F 5/04
                   128/878
7,887,471 B2 *   2/2011   McSorley .......... A63B 21/0552
                   482/136
9,737,453 B2 *   8/2017   Shimada ............ A63B 22/0046

* cited by examiner

WALKING TRAINING APPARATUS AND WALKING TRAINING METHOD THEREFOR

CROSS-REFERENCE TO RELATED APPLICATIONS

This application is based upon and claims the benefit of priority from Japanese patent application No. 2015-178278, filed on Sep. 10, 2015, the disclosure of which is incorporated herein in its entirety by reference.

BACKGROUND

1. Technical Field

The present disclosure relates to a walking training apparatus and a walking training method therefor by which a trainee (i.e., a user) does walking training.

2. Description of Related Art

A walking training apparatus by which a trainee does walking training with a walking assistance apparatus that assists a walking motion performed by the trainee being attached to his/her leg has been known (e.g., Japanese Unexamined Patent Application Publication No. 2012-095793).

Since the walking assistance apparatus has some weight, its weight becomes a burden (or a load) on the trainee to which the walking assistance apparatus is attached. Further, when the trainee performs a walking motion with the walking assistance apparatus being attached to his/her leg, the leg receives a backward inertial force from the walking assistance apparatus at a timing when the trainee starts swinging the leg forward. Therefore, there has been a problem that an excessive load is exerted on the trainee.

BRIEF SUMMARY

The present disclosure has been made in view of the above-described problem and one of the main objects thereof is to provide a walking training apparatus and a walking training method therefor capable of reducing a load on a trainee exerted at a swinging start timing while relieving (or reducing) the weight of a walking assistance apparatus.

To achieve the above-described object, a first exemplary aspect of the present disclosure is a walking training apparatus including: a walking assistance apparatus attached to a leg of a trainee, the walking assistance apparatus being configured to assist a walking motion performed by the trainee; a first wire winding mechanism for pulling a wire connected to the leg directly or through the walking assistance apparatus upward and forward by winding the wire connected to the leg, the first wire winding mechanism being configured to wind and store the wire in a leg-idling period and pull out the wire in a leg-standing period, the leg-idling period being a period in the walking motion of the trainee in which the leg is in an leg-idling state, the leg-standing period being a period in the walking motion of the trainee in which the leg is in a leg-standing state; pulling control means for reducing a weight of the walking assistance apparatus by controlling the first wire winding mechanism so that the first wire winding mechanism pulls the wire with a first pulling force; and storage amount detection means for detecting a storage amount of the wire wound and stored in the first wire winding mechanism, in which the pulling control means controls the first wire winding mechanism so that the first wire winding mechanism pulls the wire of the first wire winding mechanism with, instead of the first pulling force, a second pulling force larger than the first pulling force in a swinging start period in which the storage amount of the wire detected by the storage amount detection means is equal to or smaller than a predetermined storage amount of the wire, the predetermined storage amount being a storage amount in a period including a timing when the wire of the first wire winding mechanism changes from a pulling-out state to a winding state.

According to this aspect, the pulling control means reduces the weight of the walking assistance apparatus by controlling the first wire winding mechanism so that the first wire winding mechanism pulls the wire with the first pulling force. As a result, the weight of the walking assistance apparatus exerted on the trainee's leg can be relieved (or reduced). Further, the pulling control means controls the first wire winding mechanism so that the first wire winding mechanism pulls the wire of the first wire winding mechanism with, instead of the first pulling force, the second pulling force larger than the first pulling force in the period in which the storage amount of the wire detected by the storage amount detection means is equal to or smaller than the predetermined storage amount of the wire, the predetermined storage amount being the storage amount in the period including the timing when the wire of the first wire winding mechanism changes from the pulling-out state to the winding state. As a result, at the timing when the leg to which the walking assistance apparatus is attached starts swinging, the load caused by the above-described inertial force at the swinging start can be reduced and hence the load exerted on the leg can be reduced. That is, it is possible to reduce the load on the trainee exerted at the swinging start timing while relieving (or reducing) the weight of a walking assistance apparatus.

In this aspect, the swinging start period may be a period in which a value obtained by subtracting the storage amount of the wire detected by the storage amount detection means from a maximum wire storage amount of the first wire winding mechanism is equal to or larger than a predetermined amount of difference between the predetermined storage amount of the wire in the period including the timing when the wire of the first wire winding mechanism changes from the pulling-out state to the winding state and the maximum wire storage amount.

In this aspect, the pulling control means may update the maximum wire storage amount of the first wire winding mechanism for each leg-idling period. As a result, the leg swinging start timing can be determined more accurately and hence the load caused by the inertial force at the swinging start timing can be reduced more optimally.

In this aspect, the walking training apparatus may further include a second wire winding mechanism for pulling a wire connected to the leg directly or through the walking assistance apparatus upward and backward by winding the wire connected to the leg, the second wire winding mechanism being configured to wind and store the wire in the leg-idling period of the leg and pull out the wire in the leg-standing period of the leg, in which the pulling control means may increase a horizontally-forward component of a pulling force applied by the first and second wire winding mechanisms in the swinging start period in which the storage amount of the wire detected by the storage amount detection means is equal to or smaller than the predetermined storage amount of the wire, the predetermined storage amount being the storage amount in the period including the timing when the wire of the first wire winding mechanism changes from the pulling-out state to the winding state. As a result, the vertically-upward component and the horizontally-forward component of the pulling force applied by the first and second wire winding mechanisms can be accurately controlled independently of each other. Therefore, it is possible, at the timing when the leg to which the walking assistance apparatus is attached starts swinging, to reduce the load exerted on the leg more optimally while reducing the load caused by the gravitational force of the walking assistance apparatus.

To achieve the above-described object, another exemplary aspect of the present disclosure may be a walking training method for a walking training apparatus, the walking training apparatus including: a walking assistance apparatus attached to a leg of a trainee, the walking assistance apparatus being configured to assist a walking motion performed by the trainee; a first wire winding mechanism for pulling a wire connected to the leg directly or through the walking assistance apparatus upward and forward by winding the wire connected to the leg, the first wire winding mechanism being configured to wind and store the wire in a leg-idling period and pull out the wire in a leg-standing period, the leg-idling period being a period in the walking motion of the trainee in which the leg is in an leg-idling state, the leg-standing period being a period in the walking motion of the trainee in which the leg is in a leg-standing state; pulling control means for reducing a weight of the walking assistance apparatus by controlling the first wire winding mechanism so that the first wire winding mechanism pulls the wire with a first pulling force; and storage amount detection means for detecting a storage amount of the wire wound and stored in the first wire winding mechanism, in which the first wire winding mechanism is controlled so that the first wire winding mechanism pulls the wire of the first wire winding mechanism with, instead of the first pulling force, a second pulling force larger than the first pulling force in a swinging start period in which the storage amount of the wire detected by the storage amount detection means is equal to or smaller than a predetermined storage amount of the wire, the predetermined storage amount being a storage amount in a period including a timing when the wire of the first wire winding mechanism changes from a pulling-out state to a winding state.

According to this aspect, the weight of the walking assistance apparatus is reduced by controlling the first wire winding mechanism so that the first wire winding mechanism pulls the wire with the first pulling force. As a result, the weight of the walking assistance apparatus exerted on the trainee's leg can be relieved (or reduced). Further, the first wire winding mechanism is controlled so that the first wire winding mechanism pulls the wire of the first wire winding mechanism with, instead of the first pulling force, the second pulling force larger than the first pulling force in the period in which the storage amount of the wire detected by the storage amount detection means is equal to or smaller than the predetermined storage amount of the wire, the predetermined storage amount being the storage amount in the period including the timing when the wire of the first wire winding mechanism changes from the pulling-out state to the winding state. As a result, at the timing when the leg to which the walking assistance apparatus is attached starts swinging, the load caused by the above-described inertial force at the swinging start can be reduced and hence the load exerted on the leg can be reduced. That is, it is possible to reduce the load on the trainee exerted at the swinging start timing while relieving (or reducing) the weight of a walking assistance apparatus.

According to the present disclosure, it is possible to provide a walking training apparatus and a walking training method therefor capable of reducing a load on a trainee exerted at a swinging start timing while relieving (or reducing) the weight of a walking assistance apparatus. The above and other objects, features and advantages of the present disclosure will become more fully understood from the detailed description given hereinbelow and the accompanying drawings which are given by way of illustration only, and thus are not to be considered as limiting the present disclosure.

DETAILED DESCRIPTION

First Exemplary Embodiment

Exemplary embodiments according to the present disclosure are explained hereinafter with reference to the drawings.

Figure 1:
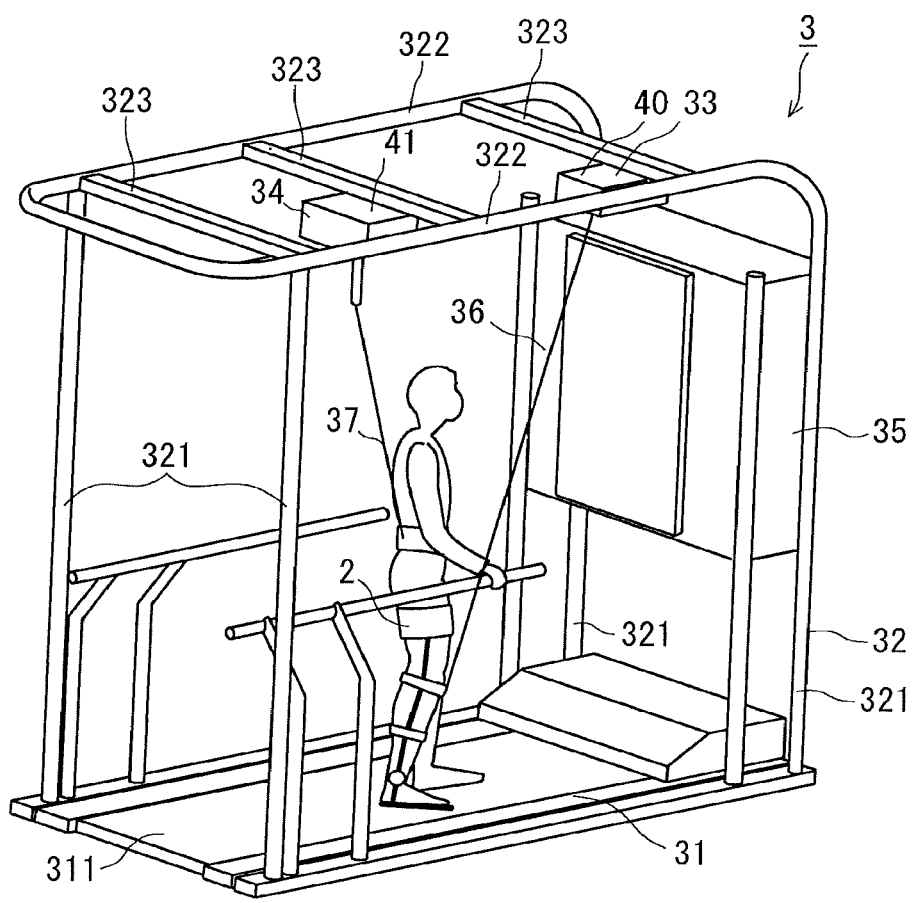
FIG. 1 is a perspective view showing a schematic configuration of a walking training apparatus according to a first exemplary embodiment of the present disclosure.

FIG. 1 is a perspective view showing a schematic configuration of a walking training apparatus according to a first exemplary embodiment of the present disclosure. A walking training apparatus 1 according to the first exemplary embodiment is, for example, an apparatus by which a trainee such as a patient having hemiplegia caused by a stroke does walking training. The walking training apparatus 1 includes a walking assistance apparatus 2 attached to the trainee's leg and a training apparatus 3 by which the trainee does walking training.

Figure 2:
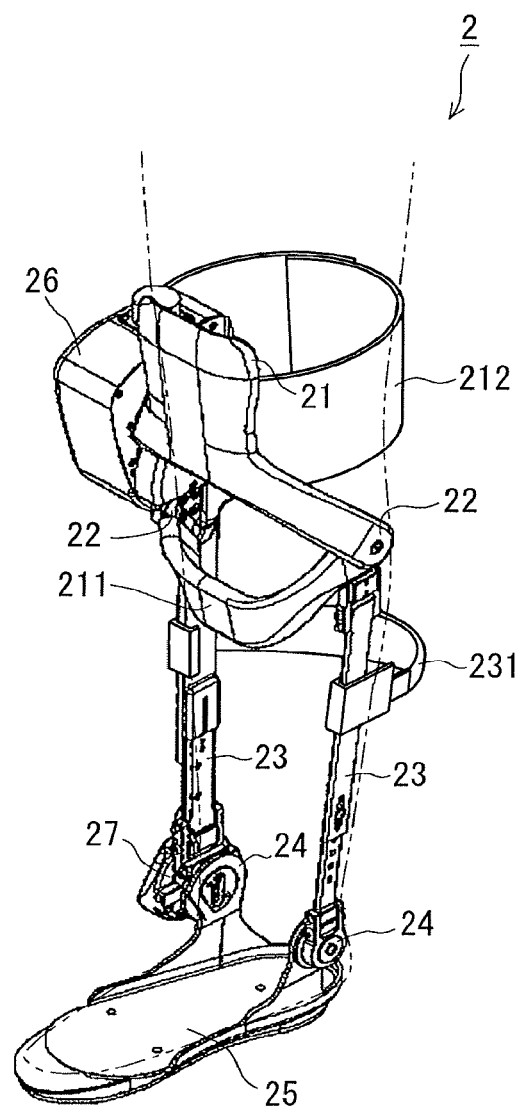
FIG. 2 is a perspective view showing a schematic configuration of a walking assistance apparatus.

The walking assistance apparatus 2 is, for example, attached to a diseased leg of a trainee who does a walking training and assists walking of the trainee (FIG. 2). The walking assistance apparatus 2 includes an upper thigh frame 21, a lower thigh frame 23 connected to the upper thigh frame 21 through a knee joint part 22, a sole frame 25 connected to the lower thigh frame 23 through an ankle joint part 24, a motor unit 26 that rotationally drives the knee joint part 22, and an adjustment mechanism 27 that adjusts the movable range of the ankle joint part 24. Note that the above-described configuration of the walking assistance apparatus 2 is merely an example and the configuration of the walking assistance apparatus 2 is not limited to such an example. For example, the walking assistance apparatus 2 may include another motor unit that rotationally drives the ankle joint part 24.

The upper thigh frame 21 is attached to the upper thigh of the trainee's leg and the lower thigh frame 23 is attached to the lower thigh of the trainee's leg. The upper thigh frame 21 is, for example, equipped with an upper thigh harness 212 for fixing the upper thigh. The upper thigh frame 21 is equipped with a horizontally-extending and horizontally-long first frame 211 for connecting with a wire 36 of a first wire winding mechanism 33 (which is described later).

Note that the above-described connecting part of the first wire winding mechanism 33 is merely an example and the connection of the first wire winding mechanism 33 is not limited to such an example. For example, the wire 36 of the first wire winding mechanism 33 may be connected to the upper thigh harness 212 and the pulling point of the first wire winding mechanism 33 can be disposed at an arbitrary position in the walking assistance apparatus 2.

The motor unit 26 rotationally drives the knee joint part 22 according to the walking motion of the trainee and thereby assists the walking of the trainee. Note that the above-described configuration of the walking assistance apparatus 2 is merely an example and the configuration of the walking assistance apparatus 2 is not limited to such an example. Any walking assistance apparatus capable of being attached to the trainee's leg and assisting walking of the trainee can be applied.

The training apparatus 3 includes a treadmill 31, a frame main body 32, first and third wire winding mechanisms 33 and 34, and a control device 35. The treadmill 31 rotates a ring-shaped belt 311. The trainee gets on the belt 311 and walks on the belt 311 according to the movement of the belt 311. By doing so, the trainee does walking training.

The frame main body 32 includes two pairs of pillar frames 321 vertically disposed on the treadmill 31, a pair of lengthwise frames 322 extending in the lengthwise direction and connected to respective pillar frames 321, and three crosswise frames 323 extending in the crosswise direction and connected to each of the lengthwise frames 322. Note that the configuration of the above-described frame main body 32 is merely an example and is not limited to this example.

In the front crosswise frame 323, the first wire winding mechanism 33 that winds the wire 36 connected to the trainee's leg directly or through the walking assistance apparatus 2 and thereby pulls the wire 36 is provided. One end of the wire 36, which is pulled by the first wire winding mechanism 33, is connected to the walking assistance apparatus 2. The first wire winding mechanism 33 pulls the walking assistance apparatus 2 upward and forward through the wire 36 by winding the wire 36.

The first wire winding mechanism 33 includes, for example, a mechanism for winding the wire 36 around a rotor and pulling the wire 36 from the rotor, a motor that drives this mechanism, and so on. The first wire winding mechanism 33 is configured so as to wind the wire 36 around the rotor and thereby store the wire 36 in a leg-idling period in the walking motion performed by the trainee in which the trainee's leg is in a leg-idling state and pull out the wire 36 from the rotor in a leg-standing period in the walking motion performed by the trainee in which the trainee's leg is in a leg-standing state.

Figure 3:
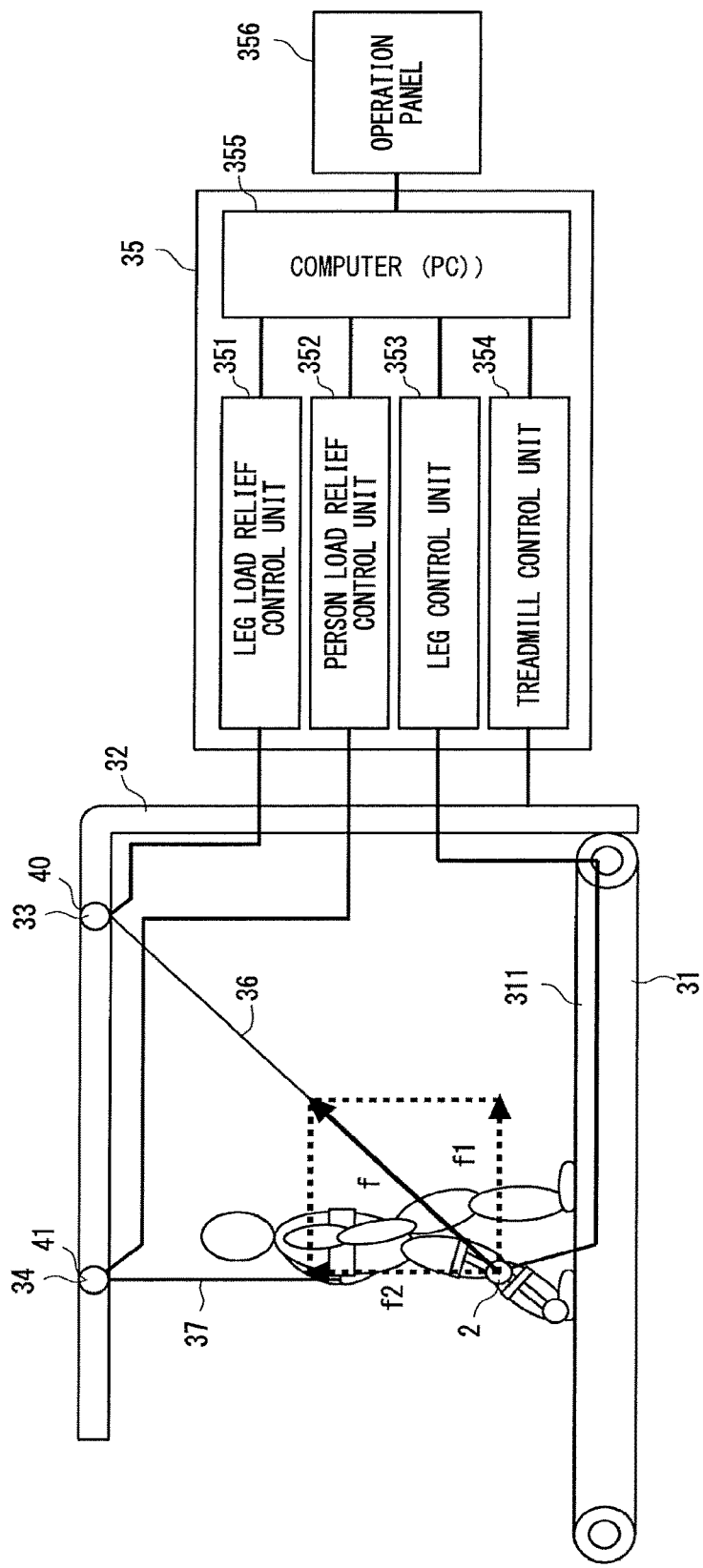
FIG. 3 is a block diagram showing a schematic system configuration of a control device according to the first exemplary embodiment of the present disclosure.

The vertically-upward component f2 of the pulling force f applied by the first wire winding mechanism 33 supports the weight of the walking assistance apparatus 2 (FIG. 3). The horizontally-forward component f1 of the pulling force f applied by the first wire winding mechanism 33 assists the start of swinging of the leg. In this way, the walking load of the trainee in the walking training can be reduced.

The third wire winding mechanism 34 is disposed in the rear crosswise frame 323 and pulls a wire 37 upward. One end of the wire 37 is connected to, for example, a belt attached to at or near the trainee's waist. The third wire winding mechanism 34 includes, for example, a mechanism for winding the wire 37 around a rotor and pulling the wire 37 from the rotor, a motor that drives this mechanism, and so on. The third wire winding mechanism 34 pulls the trainee's waist upward through the wire 37. In this way, the load on the trainee caused by the weight of the trainee himself/herself can be reduced. Each of the first and third wire winding mechanism 33 and 34 is connected to the control device 35 through a wiring line or the like.

The first and third wire winding mechanisms 33 and 34 include first and third storage amount detection units 40 and 41, respectively, that detect the storage amounts (winding amounts) of the wires 36 and 37, which are wound around the respective rotors of the first and third wire winding mechanisms 33 and 34 and thereby stored therein. The first storage amount detection unit 40 is a specific example of the storage amount detection means. The first and third storage amount detection units 40 and 41 detect, for example, the rotation angles and/or the rotation amounts of the rotors by using angle sensors and thereby detect the storage amounts of the wires 36 and 37 wound around the rotors and stored in the wire winding mechanisms. The first and third storage amount detection units 40 and 41 output the detected storage amounts of the wires 36 and 37 to the control device 35. Note that the walking training apparatus may include only the first wire winding mechanism 33.

The control device 35 is a specific example of the pulling control means. The control device 35 controls each of the pulling forces applied by the first and third wire winding mechanisms 33 and 34, the driving of the treadmill 31, and the walking assistance apparatus 2. For example, the control device 35 is formed by hardware mainly using a microcomputer including a CPU (Central Processing Unit) that performs arithmetic processing, control processing, and so on, a memory including a ROM (Read Only Memory) that stores an arithmetic program, a control program and so on to be executed by the CPU, a RAM (Random Access Memory) and so on, and an interface unit (I/F) that externally receives and outputs signals. The CPU, the memory, and the interface unit are connected with each other through a data bus or the like The control device 35 controls the first wire winding mechanism 33 so that the first wire winding mechanism 33 pulls the wire 36 with a first pulling force for reducing the weight of the walking assistance apparatus 2 during walking training. The control device 35 controls the first wire winding mechanism 33 so that, for example, the vertically-upward component of the first pulling force applied by the first wire winding mechanism 33 becomes equal to the gravitational force of the walking assistance apparatus 2 during the walking training. As a result, the load on the walking of the trainee exerted by the gravitational force of the walking assistance apparatus 2 can be reduced.

FIG. 3 is a block diagram showing a schematic system configuration of the control device according to this exemplary embodiment.

The control device 35 includes, for example, a leg load relief control unit 351 that controls the first wire winding mechanism 33, a person load relief control unit 352 that controls the third wire winding mechanism 34, a leg control unit 353 that controls the walking assistance apparatus 2, a treadmill control unit 354 that controls the treadmill 31, a computer or a PC (Personal Computer) 355 that controls these units, and an operation panel 356 for operating the computer 355. The operation panel 356 displays information such as a training instruction, a training menu, and training information (such as walking speed and biological information). The operation panel 356 is formed, for example, as a touch panel, and a user can enter various types of information through the operation panel 356.

Incidentally, since the walking assistance apparatus has some weight, its weight becomes a burden (or a load) on the trainee to which the walking assistance apparatus is attached. Further, when the trainee performs a walking motion with the walking assistance apparatus being attached to his/her leg, the leg receives a backward inertial force from the walking assistance apparatus at a timing when the trainee starts swinging the leg forward. Therefore, there has been a problem that an excessive load is exerted on the trainee.

To cope with this, in the walking training apparatus 1 according to the first exemplary embodiment, the control device 35 reduces the weight of the walking assistance apparatus 2 by controlling the first wire winding mechanism 33 so that the first wire winding mechanism 33 pulls the wire 36 with the first pulling force. As a result, the weight of the walking assistance apparatus exerted on the trainee's leg can be relieved (or reduced). Further, the control device 35 determines a timing when the leg to which the walking assistance apparatus 2 is attached starts swinging and increases the pulling force applied by the first wire winding mechanism 33 from the first pulling force to a second pulling force larger than the first pulling force at this swinging start timing. As a result, at the timing when the leg to which the walking assistance apparatus 2 is attached starts swinging, the load caused by the above-described inertial force at the swinging start can be reduced and hence the load exerted on the leg can be reduced. That is, it is possible to reduce the load on the trainee exerted at the swinging start timing while relieving (or reducing) the weight of the walking assistance apparatus 2.

Figure 4:
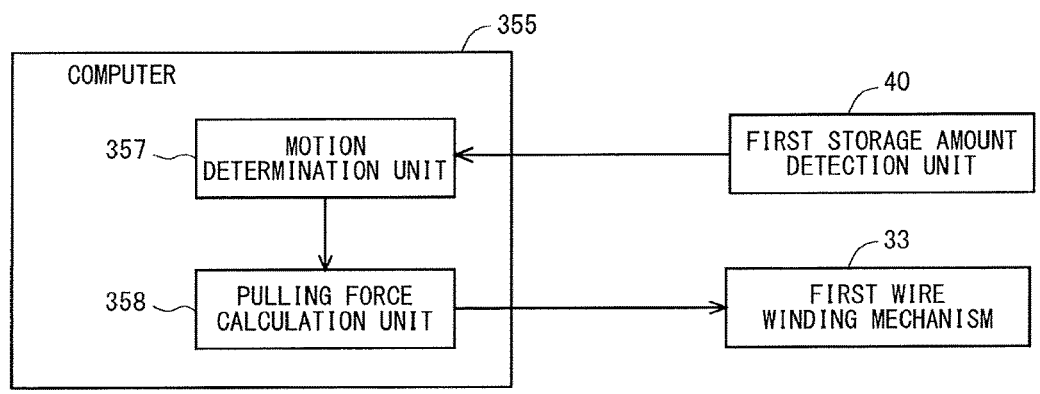
FIG. 4 is a block diagram showing a schematic system configuration of a computer according to the first exemplary embodiment of the present disclosure.

FIG. 4 is a block diagram showing a schematic system configuration of a computer according to the first exemplary embodiment. A computer 355 according to the first exemplary embodiment includes a motion determination unit 357 that determines a timing when the leg to which the walking assistance apparatus 2 is attached starts swinging, and a pulling-force calculation unit 358 that increases the pulling force applied by the first wire winding mechanism from the first pulling force to a second pulling force larger than the first pulling force at the swinging start timing.

The motion determination unit 357 determines the timing (period) at which the leg to which the walking assistance apparatus 2 is attached starts swinging forward based on the wire storage amount detected by the first storage amount detection unit 40.

Figure 5:
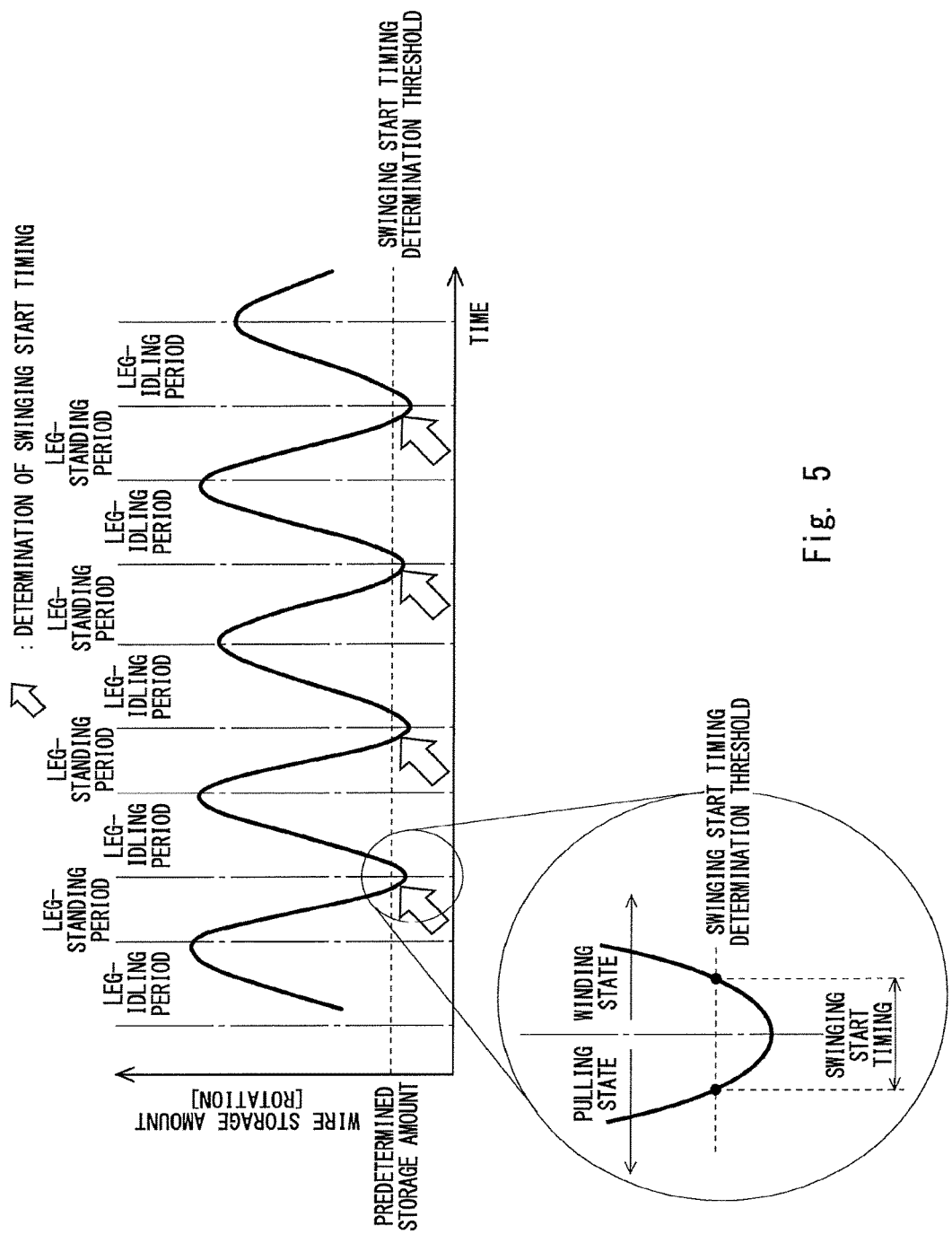
FIG. 5 is a graph showing an example of a relation between wire storage amounts and leg-idling and leg-standing periods.

FIG. 5 is a graph showing an example of a relation between wire storage amounts and leg-idling and leg-standing periods. As shown in FIG. 5, it can be seen that leg-idling periods and leg-standing periods alternately occur in a walking motion performed by a trainee. Further, the wire storage amount increases and decreases roughly in a cyclic fashion according to these periods. Further, the timing when the leg starts swinging forward (hereinafter also called a "leg forward swinging start timing") corresponds to the timing when the wire 36 of the first wire winding mechanism 33 changes from a pulling-out state to a winding state and also corresponds to the timing when the trainee's leg changes from a leg-idling period to a leg-standing period. This timing occurs roughly in a cyclic fashion.

In the first exemplary embodiment, for example, the motion determination unit 357 determines a period in which the wire storage amount detected by the first storage amount detection unit 40 becomes equal to or smaller than a predetermined storage amount (hereinafter also called a "swinging start timing determination threshold"), which is a storage amount in a period including a timing when the wire 36 of the first wire winding mechanism 33 changes from a pulling-out state to a winding state, as a timing when the leg starts swinging forward.

For example, it is possible to experimentally obtain a timing when the wire 36 of the first wire winding mechanism 33 changes from a pulling-out state to a winding state in advance. Then, a wire storage amount in a period including this state-change timing is obtained and set (i.e., stored) as the swinging start timing determination threshold in the aforementioned memory or the like.

Note that this swinging start timing determination threshold is configured so that, for example, a user can arbitrarily change its setting through an operation panel 356, an operation terminal, or the like. For example, an optimal value of this swinging start timing determination threshold may be determined based on the characteristics of a trainee (such as the step of a trainee and a physical ability of a trainee), the moving speed of the belt 311 of the treadmill 31, and the like. However, the swinging start timing determination threshold should be equal to or greater than the wire storage amount at the timing when the wire 36 of the first wire winding mechanism 33 changes from a pulling-out state to a winding state. When the swinging start timing determination threshold is raised, the motion determination unit 357 determines the swinging start timing at an earlier timing than the original timing and determines it over a longer period than the original period. Therefore, the second pulling force, which is defined to be larger than the first pulling force, is applied to the wire 36 of the first wire winding mechanism 33 at an earlier timing and over a longer period.

The motion determination unit 357 determines that it is the timing when the leg starts swinging forward when the wire storage amount detected by the first storage amount detection unit 40 becomes equal to or smaller than the above-defined swinging start timing determination threshold. The motion determination unit 357 outputs a determination signal to the pulling-force calculation unit 358 while the motion determination unit 357 determines that it is the timing when the leg to which the walking assistance apparatus 2 is attached starts swinging forward.

The pulling-force calculation unit 358 calculates a first pulling force command value for the first wire winding mechanism 33 and outputs the calculated first pulling force command value to the first wire winding mechanism 33. The first wire winding mechanism 33 pulls the wire 36 connected to the walking assistance apparatus 2 by a first pulling force f according to the first pulling force command value output from the pulling-force calculation unit 358. At this point, the vertically-upward component f2 of the first pulling force f applied by the first wire winding mechanism 33 supports the weight of the walking assistance apparatus 2. The horizontally-forward component f1 of the first pulling force f applied by the first wire winding mechanism 33 assists the start of swinging of the leg. That is, the first pulling force command value is set so that, for the normal walking motion performed by the user, the vertically-upward component f2 of the first pulling force f supports the weight of the walking assistance apparatus 2 and the horizontally-forward component f1 of the first pulling force f optimally assists the start of swinging of the leg at the same time.

However, as described above, the leg receives a backward inertial force from the walking assistance apparatus 2 at the leg swinging start timing in the walking and a load larger than that in the normal walking motion is exerted on the trainee's leg at this swinging start timing. To cope with this, the pulling-force calculation unit 358 according to the first exemplary embodiment increases the pulling force command value from the first pulling force command value to a second pulling force command value when it receives the determination signal from the motion determination unit 357. The first wire winding mechanism 33 pulls the wire 36 connected to the walking assistance apparatus 2 according to the second pulling force command value output from the pulling-force calculation unit 358.

In this way, the pulling force applied by the first wire winding mechanism 33 is increased form the first pulling force to the second pulling force only when the inertial force is exerted at the leg swinging start timing. As a result, the load caused by the inertial force at the leg swinging start timing can be reduced.

Figure 6:
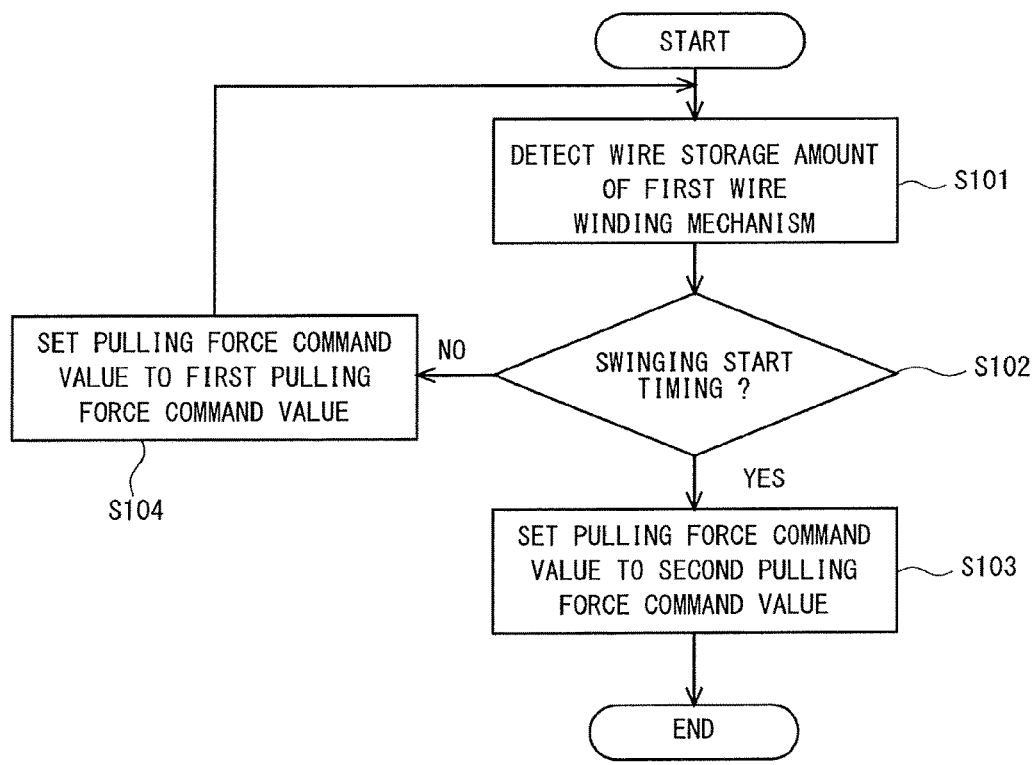
FIG. 6 is a flowchart showing a flow of a walking training method according to the first exemplary embodiment of the present disclosure.

FIG. 6 is a flowchart showing a flow of a walking training method according to the first exemplary embodiment. Note the processes shown in FIG. 6 are repeatedly performed at predetermined intervals.

The first storage amount detection unit 40 detects the amount of the wire wound around the rotor and stored in the first wire winding mechanism 33, and outputs the detected wire storage amount to the control device 35 (step S101).

The motion determination unit 357 determines whether or not it is a timing when the leg to which the walking assistance apparatus 2 is attached starts swinging forward based on the wire storage amount detected by the first storage amount detection unit 40 (step S102).

When the motion determination unit 357 determines that it is the timing when the leg to which the walking assistance apparatus 2 is attached starts swinging forward (Yes at step S102), the pulling-force calculation unit 358 sets the pulling force command value to the second pulling force command value and outputs the set second pulling force command value to the first wire winding mechanism 33 (step S103). On the other hand, when the motion determination unit 357 determines that it is not the timing when the leg to which the walking assistance apparatus 2 is attached starts swinging forward (No at step S102), the pulling-force calculation unit 358 sets the pulling force command value to the first pulling force command value and outputs the set first pulling force command value to the first wire winding mechanism 33 (step S104).

As described above, in the first exemplary embodiment, the control device 35 reduces the weight of the walking assistance apparatus 2 by controlling the first wire winding mechanism 33 so that the first wire winding mechanism 33 pulls the wire 36 with the first pulling force. As a result, the weight of the walking assistance apparatus 2 exerted on the trainee's leg can be relieved (or reduced). Further, the control device 35 controls the first wire winding mechanism 33 so that the first wire winding mechanism 33 pulls the wire 36 of the first wire winding mechanism 33 with, instead of the first pulling force, the second pulling force larger than the first pulling force in the period in which the storage amount of the wire 36 detected by the first storage amount detection unit 40 is equal to or smaller than the predetermined storage amount of the wire 36, which is the storage amount in the period including the timing when the wire 36 of the first wire winding mechanism 33 changes from the pulling-out state to the winding state. As a result, at the timing when the leg to which the walking assistance apparatus 2 is attached starts swinging, the load caused by the above-described inertial force at the swinging start can be reduced and hence the load exerted on the leg can be reduced. That is, it is possible to reduce the load on the trainee exerted at the swinging start timing while relieving (or reducing) the weight of a walking assistance apparatus 2.

Second Exemplary Embodiment

Figure 7:
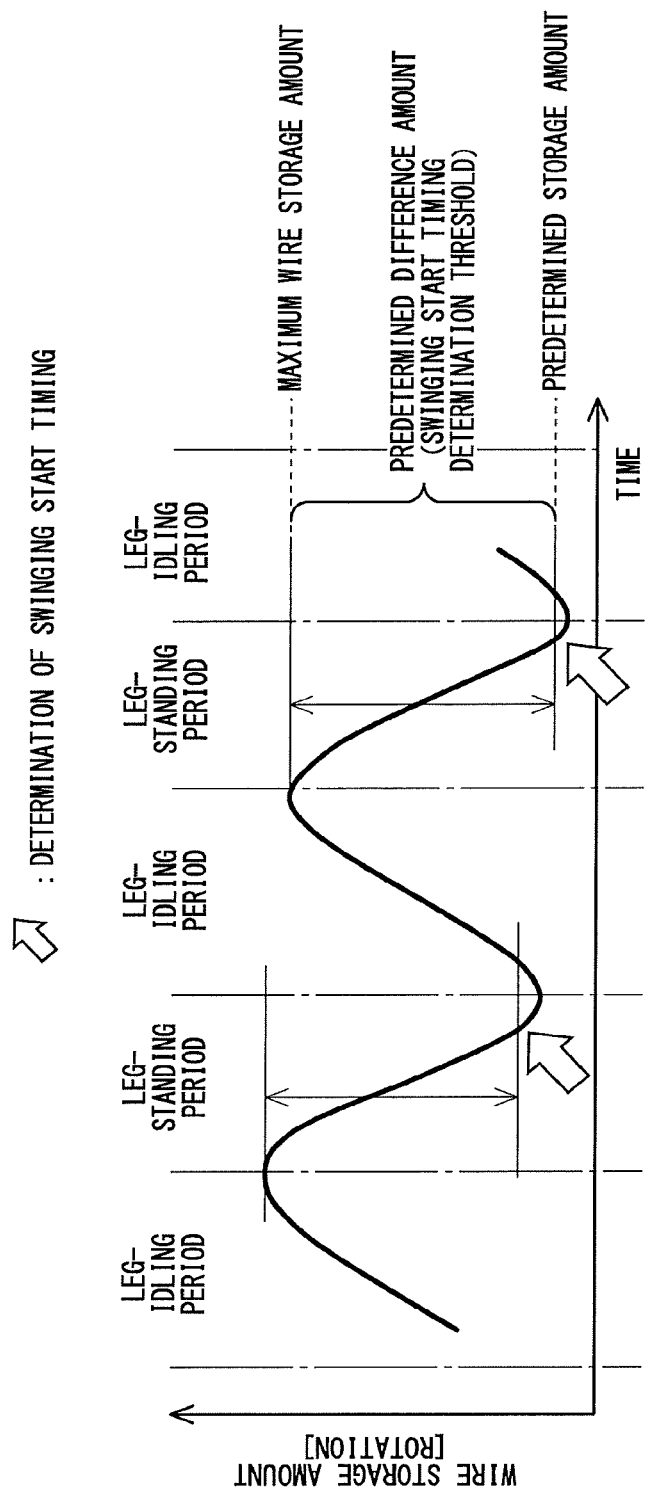
FIG. 7 is a graph showing an example of a difference amount between a predetermined wire storage amount and a maximum wire storage amount in a period including a timing when the wire changes from a pulling-out state to a winding state.

In a second exemplary embodiment of the present disclosure, a difference amount between a predetermined storage amount of the wire 36 of the first wire winding mechanism 33, which is a storage amount in a period including a timing when the wire 36 changes from a pulling-out state to a winding state, and a maximum wire storage amount is set (i.e., stored) as the swinging start timing determination threshold in the aforementioned memory or the like (FIG. 7). The aforementioned maximum wire storage amount is, for example, a wire storage amount at the timing when the wire 36 of the first wire winding mechanism 33 changes from a winding state to a pulling-out state. Further, the maximum wire storage amount is, for example, experimentally obtained and stored in aforementioned memory or the like in advance.

In this case, the motion determination unit 357 determines that it is a timing when the trainee's leg starts swinging forward when a value obtained by subtracting the storage amount of the wire 36 detected by the first storage amount detection unit 40 from the maximum wire storage amount is determined to be equal to or larger than the swinging start timing determination threshold.

Note that there is a possibility that the wire storage amount changes for each leg-idling period (i.e., changes from one leg-idling period to another leg-idling period. Therefore, there is a possibility that the maximum wire storage amount changes for each leg-idling period. Accordingly, the motion determination unit 357 may update the maximum wire storage amount stored in the aforementioned memory for each leg-idling period. In this way, the leg swinging start timing can be determined more accurately and hence the load caused by the inertial force at the swinging start timing can be reduced more optimally.

Figure 8:
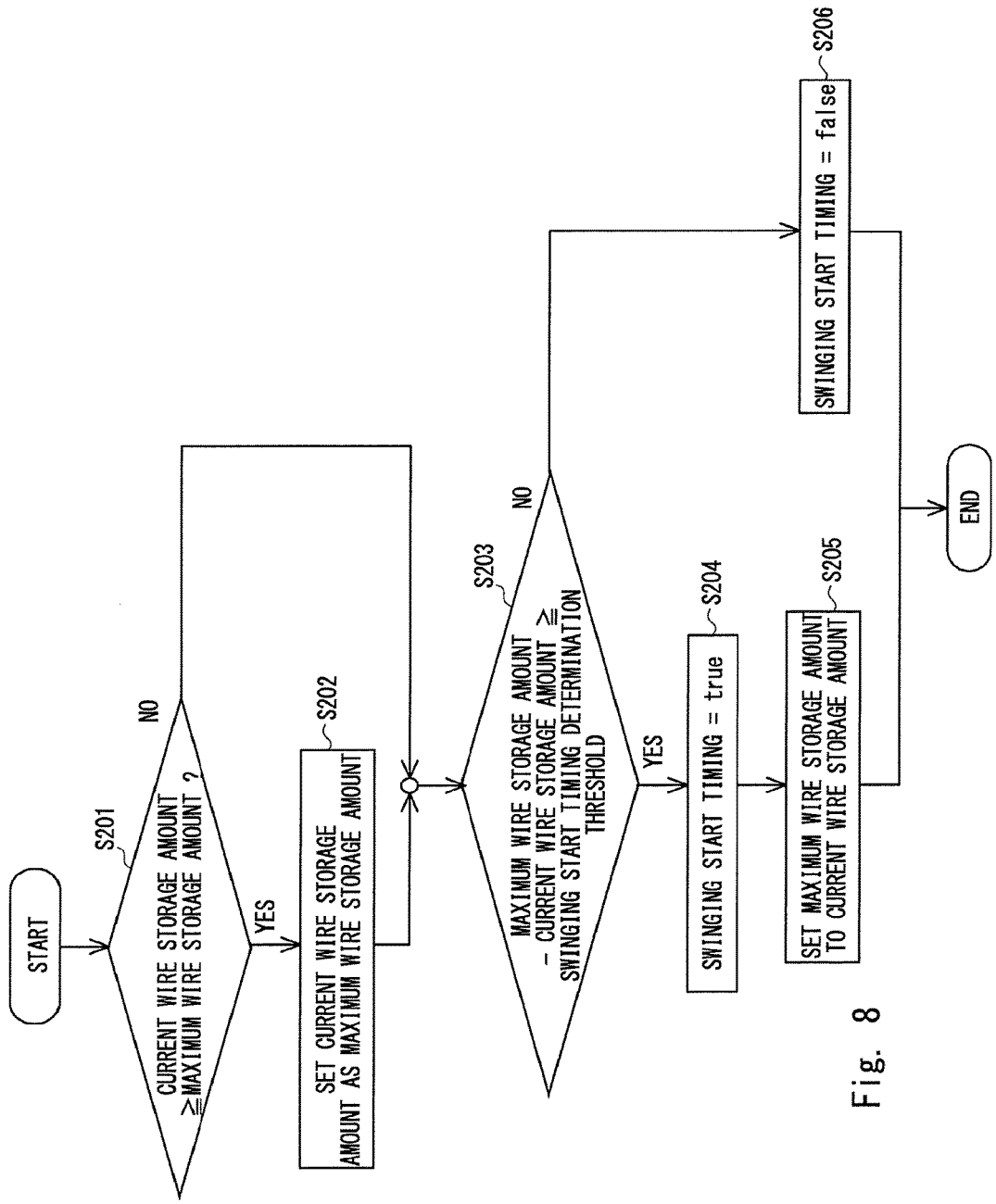
FIG. 8 is a flowchart showing an example of a process flow for updating a maximum wire storage amount in each leg-idling period and determining a swinging start timing.

FIG. 8 is a flowchart showing an example of a process flow for updating the maximum wire storage amount for each leg-idling period and determining the swinging start timing. Note the processes shown in FIG. 8 are repeatedly performed at predetermined intervals.

The motion determination unit 357 determines whether or not the current wire storage amount detected by the first storage amount detection unit 40 is equal to or larger than the maximum wire storage amount set in the aforementioned memory (step S201).

When the motion determination unit 357 determines that the current wire storage amount detected by the first storage amount detection unit 40 is equal to or larger than the maximum wire storage amount set in the aforementioned memory (Yes at step S201), the motion determination unit 357 resets that current wire storage amount detected by the first storage amount detection unit 40 as a new maximum wire storage amount in the aforementioned memory (i.e. updates the maximum wire storage amount by the current wire storage amount detected by the first storage amount detection unit 40) (step S202) and proceeds to the process in the later-described step S203. When the motion determination unit 357 determines that the current wire storage amount detected by the first storage amount detection unit 40 is not equal to or larger than the maximum wire storage amount set in the aforementioned memory (No at step S201), the motion determination unit 357 proceeds to the process in the later-described step S203 (without updating the maximum wire storage amount).

The motion determination unit 357 determines whether or not a value obtained by subtracting the current wire storage amount detected by the first storage amount detection unit 40 from the maximum wire storage amount is equal to or larger than the swinging start timing determination threshold (step S203). When the motion determination unit 357 determines that the value obtained by subtracting the current wire storage amount detected by the first storage amount detection unit 40 from the maximum wire storage amount is equal to or larger than the swinging start timing determination threshold (Yes at step S203), the motion determination unit 357 determines that it is the timing when the leg starts swinging forward (True) (step S204). The motion determination unit 357 sets the maximum wire storage amount to the current wire storage amount of the first wire winding mechanism 33 (i.e., updates the maximum wire storage amount by the current wire storage amount) (step S205). In this way, it is possible to temporarily reset the maximum wire storage amount set in the memory after the determination of the swinging start timing.

On the other hand, when the motion determination unit 357 determines that the value obtained by subtracting the current wire storage amount detected by the first storage amount detection unit 40 from the maximum wire storage amount is not equal to or larger than the swinging start timing determination threshold (No at step S203), the motion determination unit 357 determines that it is not the timing when the leg starts swinging forward (False) (step S206).

Note that the present disclosure is not limited to the above-described exemplary embodiments, and various modifications can be made without departing from the spirit and scope of the present disclosure.

Figure 9:
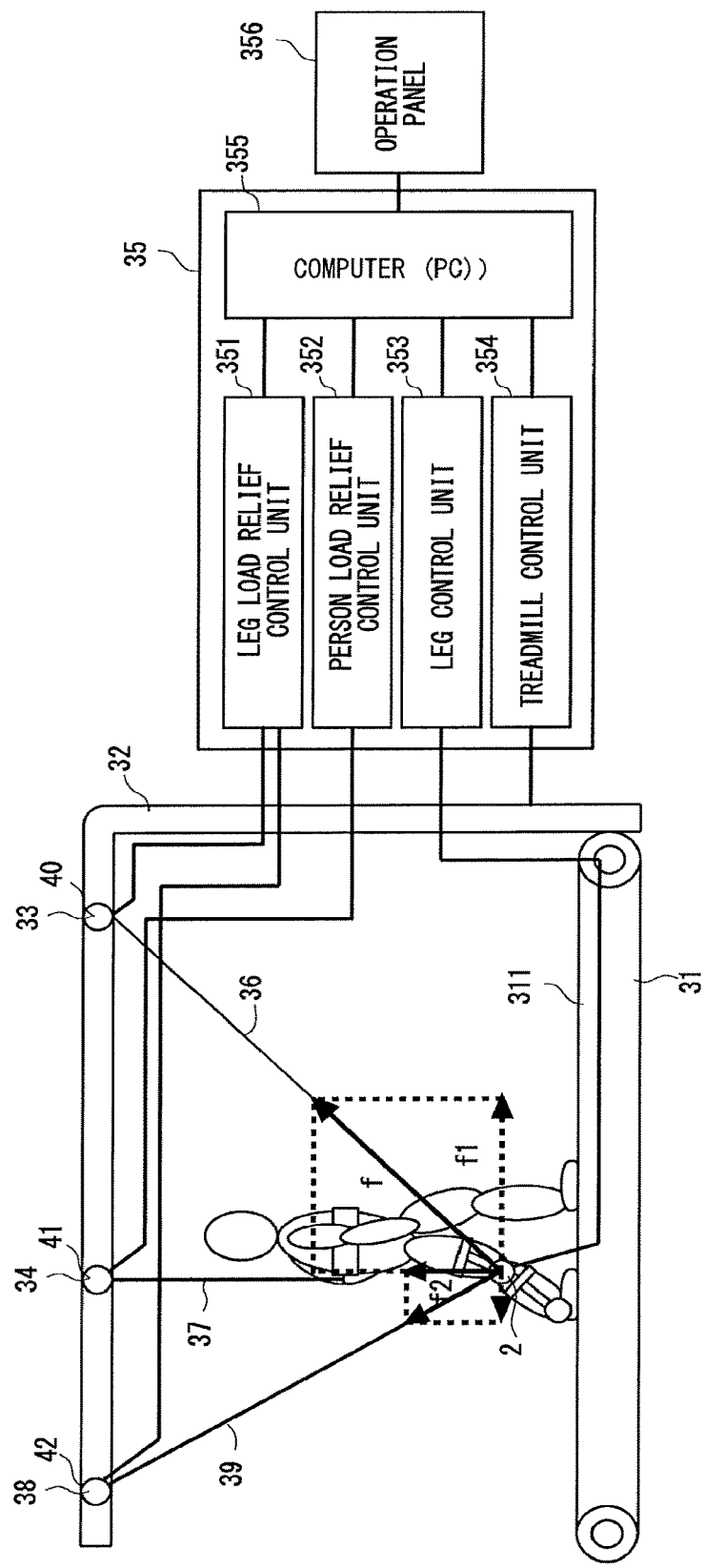
FIG. 9 is a diagram showing an example of a configuration in which a second wire winding mechanism is provided in a frame main body.

The above-described exemplary embodiment may have a configuration in which a second wire winding mechanism 38 that pulls the walking assistance apparatus 2 upward and backward through a wire 39 is provided in the crosswise frame 323 of the frame main body 32 (FIG. 9). The resultant force of the vertically-upward components of the pulling forces applied by the first and second wire winding mechanisms 33 and 38 supports the weight of the walking assistance apparatus 2. Further, the resultant force of the horizontal components of the pulling forces applied by the first and second wire winding mechanisms 33 and 38 assists the start of swinging of the leg.

The pulling force calculation unit 358 outputs a pulling force command value that makes the resultant force of the vertically-upward components of the pulling forces applied by the first and second wire winding mechanisms 33 and 38 reduce the gravitational force of the walking assistance apparatus 2 to the first and second wire winding mechanisms 33 and 38.

Further, when the pulling-force calculation unit 358 receives the determination signal from the motion determination unit 357, the pulling-force calculation unit 358 increases the pulling force command value from the first pulling force command value to the second pulling force command value and outputs the increased pulling force command value to the first wire winding mechanism 33. At this point, the pulling force calculation unit 358 is outputting the normal first pulling force command value (pulling force command value=constant) to the second wire winding mechanism 38. However, the present disclosure is not limited to such a configuration and method. That is, the pulling force command value for the second wire winding mechanism 38 may be changed in a manner similar to the first pulling force command value for the first wire winding mechanism 33. In other words, the pulling force calculation unit 358 changes the pulling force command values for the first and second wire winding mechanisms 33 and 38 and thereby increases the horizontally-forward components of the pulling forces applied by the first and second wire winding mechanisms 33 and 38 at the swinging start timing. In this way, the vertically-upward components and the horizontally-forward components of the pulling forces applied by the first and second wire winding mechanisms 33 and 38 can be accurately controlled independently of each other. As a result, it is possible to, while reducing the load caused by the gravitational force of the walking assistance apparatus, reduce the load exerted on the leg to which the walking assistance apparatus 2 is attached at the start of swinging of that leg more optimally.

Further, in the above-described exemplary embodiments, the motion determination unit 357 determines that it is the timing when the leg starts swinging forward when the wire storage amount of the first wire winding mechanism 33 detected by the first storage amount detection unit 40 disposed in the first wire winding mechanism 33 becomes equal to or smaller than the set swinging start timing determination threshold. However, the present disclosure is not limited to such a configuration and method. The motion determination unit 357 may determine that it is the timing when the leg starts swinging forward when the wire storage amount of the second wire winding mechanism 38 detected by a second storage amount detection unit 42 disposed in the second wire winding mechanism 38 becomes equal to or smaller than a set swinging start timing determination threshold.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims

What is claimed is:
1. A walking training apparatus comprising:
a walking assistance apparatus configured to be attached to a leg of a trainee, the walking assistance apparatus being configured to assist a walking motion performed by the trainee;
a first wire winding mechanism that pulls a wire connected to the leg directly or through the walking assistance apparatus upward and forward by winding the wire connected to the leg, the first wire winding mechanism being configured to wind and store the wire around a rotor in a leg-idling period and pull out the wire in a leg-standing period, the leg-idling period being a period in the walking motion of the trainee in which the leg is in an leg-idling state, the leg-standing period being a period in the walking motion of the trainee in which the leg is in a leg-standing state;

pulling control means for reducing a weight of the walking assistance apparatus by controlling the first wire winding mechanism so that the first wire winding mechanism pulls the wire with a first pulling force; and storage amount detection means for detecting a storage amount of the wire wound and stored in the first wire winding mechanism based on a rotation angle or rotation amount of the rotor, wherein the pulling control means controls the first wire winding mechanism so that the first wire winding mechanism pulls the wire of the first wire winding mechanism with a second pulling force larger than the first pulling force in a swinging start period in which the storage amount of the wire detected by the storage amount detection means is equal to or smaller than a predetermined storage amount of the wire, the predetermined storage amount being a storage amount in a period including a timing when the wire of the first wire winding mechanism changes from a pulling-out state to a winding state.

2. The walking training apparatus according to claim 1, wherein the swinging start period is a period in which a value obtained by subtracting the storage amount of the wire detected by the storage amount detection means from a maximum wire storage amount of the first wire winding mechanism is equal to or larger than a predetermined amount of difference between the predetermined storage amount of the wire in the period including the timing when the wire of the first wire winding mechanism changes from the pulling-out state to the winding state and the maximum wire storage amount.

3. The walking training apparatus according to claim 2, wherein the pulling control means updates the maximum wire storage amount of the first wire winding mechanism for each leg-idling period.

4. The walking training apparatus according to claim 1, wherein the wire is a first wire, the walking training apparatus further comprises a second wire winding mechanism that pulls a second wire connected to the leg directly or through the walking assistance apparatus upward and backward by winding the second wire connected to the leg, the second wire winding mechanism being configured to wind and store the second wire in the leg-idling period of the leg and pull out the wire in the leg-standing period of the leg, and the pulling control means increases a horizontally-forward component of a pulling force applied by the first and second wire winding mechanisms in the swinging start period in which the storage amount of the first wire detected by the storage amount detection means is equal to or smaller than the predetermined storage amount of the first wire, the predetermined storage amount being a storage amount in the period including the timing when the first wire of the first wire winding mechanism changes from the pulling-out state to the winding state.

5. A walking training apparatus comprising:

a walking assistance apparatus configured to be attached to a leg of a trainee, the walking assistance apparatus being configured to assist a walking motion performed by the trainee;

a first wire winding mechanism that pulls a wire connected to the leg directly or through the walking assistance apparatus upward and forward by winding the wire connected to the leg, the first wire winding mechanism being configured to wind and store the wire around a rotor in a leg-idling period and pull out the wire in a leg-standing period, the leg-idling period being a period in the walking motion of the trainee in which the leg is in an leg-idling state, the leg-standing period being a period in the walking motion of the trainee in which the leg is in a leg-standing state;

a controller that reduces a weight of the walking assistance apparatus by controlling the first wire winding mechanism so that the first wire winding mechanism pulls the wire with a first pulling force; and a storage amount detector that detects a storage amount of the wire wound and stored in the first wire winding mechanism based on a rotation angle or rotation amount of the rotor, wherein the controller controls the first wire winding mechanism so that the first wire winding mechanism pulls the wire of the first wire winding mechanism with, instead of the first pulling force, a second pulling force larger than the first pulling force in a swinging start period in which the storage amount of the wire detected by the storage amount detector is equal to or smaller than a predetermined storage amount of the wire, the predetermined storage amount being a storage amount in a period including a timing when the wire of the first wire winding mechanism changes from a pulling-out state to a winding state.

6. The walking training apparatus according to claim 5, wherein the swinging start period is a period in which a value obtained by subtracting the storage amount of the wire detected by the storage amount detector from a maximum wire storage amount of the first wire winding mechanism is equal to or larger than a predetermined amount of difference between the predetermined storage amount of the wire in the period including the timing when the wire of the first wire winding mechanism changes from the pulling-out state to the winding state and the maximum wire storage amount.

7. The walking training apparatus according to claim 6, wherein the controller updates the maximum wire storage amount of the first wire winding mechanism for each leg-idling period.

8. The walking training apparatus according to claim 5, wherein the wire is a first wire, the walking training apparatus further comprises a second wire winding mechanism that pulls a second wire connected to the leg directly or through the walking assistance apparatus upward and backward by winding the second wire connected to the leg, the second wire winding mechanism being configured to wind and store the second wire in the leg-idling period of the leg and pull out the wire in the leg-standing period of the leg, and the controller increases a horizontally-forward component of a pulling force applied by the first and second wire winding mechanisms in the swinging start period in which the storage amount of the first wire detected by the storage amount detector is equal to or smaller than the predetermined storage amount of the first wire, the predetermined storage amount being a storage amount in the period including the timing when the first wire of the first wire winding mechanism changes from the pulling-out state to the winding state.

* * * * *